United States Patent [19]
Cabib et al.

[11] Patent Number: 5,539,517
[45] Date of Patent: Jul. 23, 1996

[54] METHOD FOR SIMULTANEOUSLY MEASURING THE SPECTRAL INTENSITY AS A FUNCTION OF WAVELENGTH OF ALL THE PIXELS OF A TWO DIMENSIONAL SCENE

[75] Inventors: Dario Cabib, Timrat; Zvi Friedman, Kiryat Bialik; Stephen G. Lipson, Kaufman; Robert A. Buckwald, Ramat Ishay, all of Israel

[73] Assignee: Numetrix Ltd., Migdal Hacmek, Israel

[21] Appl. No.: 392,019

[22] Filed: Feb. 21, 1995

Related U.S. Application Data

[63] Continuation of Ser. No. 107,673, filed as PCT/US92/01171, Feb. 19, 1992, abandoned.

[51] Int. Cl.⁶ .................................................. G01B 9/02
[52] U.S. Cl. ............................................. 356/346; 356/345
[58] Field of Search .................................... 356/346, 318, 356/345

[56] References Cited

U.S. PATENT DOCUMENTS

| | | |
|---|---|---|
| 3,504,975 | 4/1970 | White. |
| 3,684,379 | 8/1972 | Girard. |
| 3,753,619 | 8/1973 | Thorpe et al.. |
| 3,795,448 | 3/1974 | Fletcher et al.. |
| 3,915,573 | 10/1975 | Knoll et al.. |
| 4,009,962 | 3/1977 | Lauer et al.. |
| 4,014,614 | 3/1977 | Sandercock. |
| 4,076,422 | 2/1978 | Kohno. |
| 4,128,337 | 12/1978 | Zehnpfennig. |
| 4,131,792 | 12/1978 | Schlossberg. |
| 4,165,938 | 8/1979 | Doyle. |
| 4,523,846 | 6/1985 | Breckenridge et al.. |
| 4,575,248 | 3/1986 | Horwitz et al.. |
| 4,653,869 | 3/1987 | Gottlieb et al.. |
| 4,678,332 | 7/1987 | Rock et al.. |
| 4,735,507 | 4/1988 | Crane, Jr. et al.. |
| 4,743,114 | 5/1988 | Crane, Jr.. |
| 4,818,110 | 4/1989 | Davidson. |
| 4,845,558 | 7/1989 | Tsai et al.. |
| 4,926,489 | 5/1990 | Danielson et al.. |
| 4,976,542 | 12/1990 | Smith .................................. 356/346 |
| 5,030,008 | 7/1991 | Scott et al.. |
| 5,039,855 | 8/1991 | Kemeny et al.. |
| 5,048,959 | 9/1991 | Morris et al.. |
| 5,059,027 | 10/1991 | Roesler et al.. |
| 5,216,484 | 6/1993 | Chao et al.. |
| 5,377,003 | 12/1994 | Lewis et al.. |

FOREIGN PATENT DOCUMENTS

| | | |
|---|---|---|
| 0426182A2 | 10/1990 | European Pat. Off.. |
| 0426166A2 | 10/1990 | European Pat. Off.. |
| 58-214129A | 12/1983 | Japan. |
| 60-80821A | 5/1985 | Japan. |
| 126513(A) | 10/1989 | Japan. |

OTHER PUBLICATIONS

Yu, J. et al., "Acousto–Optic Tunable Filter (AOTF) Imaging Spectrometer for NASA: System Issues", SPIE vol. 1347 Optical Information Processing Systems and Architecture pp. 644–654.

(List continued on next page.)

Primary Examiner—Samuel A. Turner
Attorney, Agent, or Firm—Mark M. Friedman

[57] ABSTRACT

A method of analyzing an optical image of a scene to determine the spectral intensity of each pixel of the scene, which includes collecting incident light from the scene; (b) passing the light through an interferometer which outputs modulated light corresponding to a predetermined set of linear combinations of the spectral intensity of the light emitted from each pixel; focusing the light outputted from the interferometer on a detector array; and processing the output of the detector array to determine the spectral intensity of each pixel thereof. If the interferometer is of the moving type scanning in one dimension is required where the detector array is one dimensional, and no scanning when the detector array is two-dimensional. If the interferometer is of the non-moving type scanning is required in one dimension when the detector array is two-dimensional, and in two dimensions when the detector array is one-dimensional.

22 Claims, 9 Drawing Sheets

OTHER PUBLICATIONS

Goetz, A. et al., "Imaging Spectrometry for Earth Remote Sensing", Science, vol. 228 No. 4704 (1985).

Levin, Ira et al., "Fourier Transform Raman Spectroscopy of Biological Materials", Analytical Chemistry vol. 62 No. 21 (1990).

Treado, P. J. et al., "Multichannel Hadamard Transform Raman Microscopy", Applied Spectroscopy vol. 44 No. 1 pp. 1–4 (1990).

Kurtz, I. et al. "Rapid Scanning Fluoresence Spectroscopy Using an Acousto-Optic Tunable Filter", Rev. Sci. Instrum. 58(11) pp. 1996–2003.

Bilhorn, R. B. et al. "Spectrochemical Measurements with Multichannel Integrating Detectors", Applied Spectroscopy vol. 41 No. 7 pp. 1125–1136 (1987).

Wellman, John B., "Imaging Spectrometers for Terrestrial and Planetary Remote Sensing: A Progress Report", SPIE vol. Infrared Systems and Components 750 pp. 140–152.

Born, M. et al., "Principles of Optics" 6th Ed., Pergamon Press.

Treado, P. J. et al., "Near-Infrared Acousto-optic Filtered Spectroscope Microscopy: A Solid-State Approach to Chemical Imaging", Applied Spectroscopy, vol. 46 No. 4 pp. 553–559.

Gottlieb, M. et al. "Programmable Acousto-Optic Filter-A Device for Multispectral Optical Processing", SPIE vol. 232 International Optical Computing Conference pp. 33–42.

Chao, T. et al., "sto-Optic Tunable Filter (AOTF) Imaging Spectrometer for NASA Applications: Breadboard Demonstration", SPIE vol. 1347 Optical Information Processing Systems and Architecture II pp. 655–663.

"Acousto-Optics: From AOTFs to Optical Computers?", OE Reports, SPIE.

Bennett, C. L. et al., "Imaging Fourier Transform Spectrometer", SPIE.

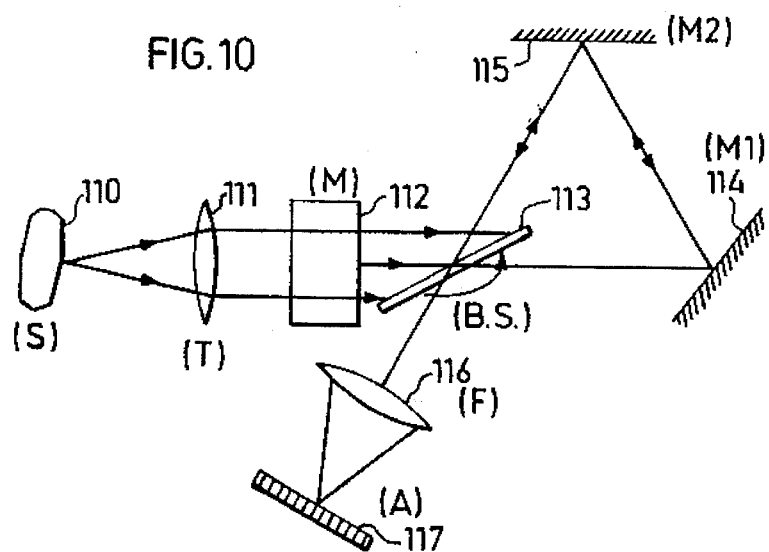
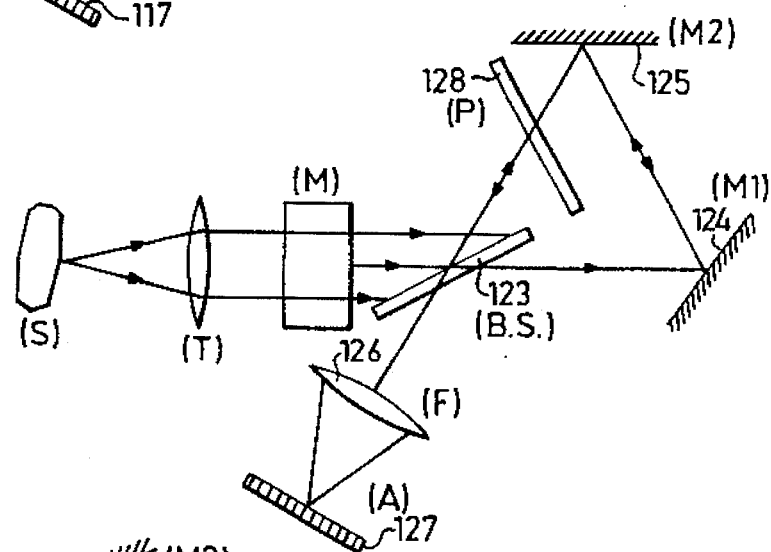
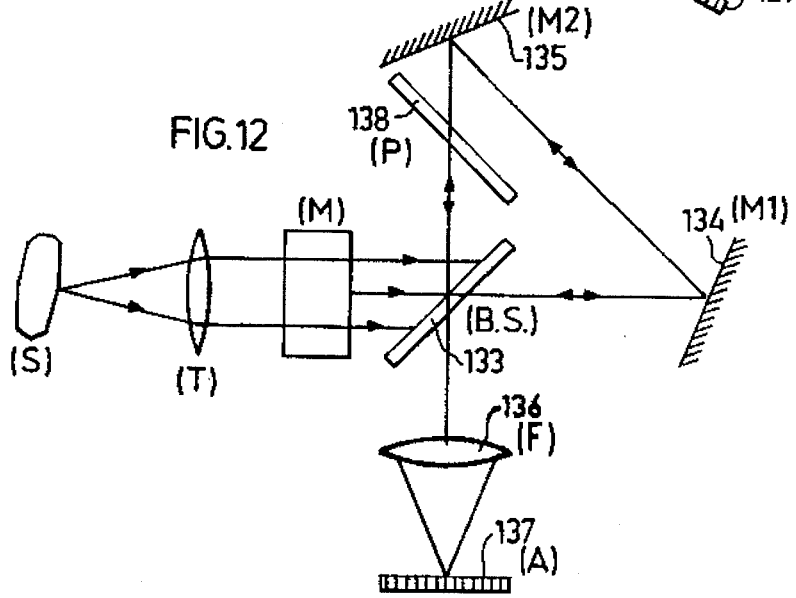

METHOD FOR SIMULTANEOUSLY MEASURING THE SPECTRAL INTENSITY AS A FUNCTION OF WAVELENGTH OF ALL THE PIXELS OF A TWO DIMENSIONAL SCENE

This is a continuation of U.S. patent application Ser. No. 08/107,673, filed as PCT/US92/01171, Feb. 19, 1992, and now abandoned.

FIELD AND BACKGROUND OF THE INVENTION

The present invention relates to a method and apparatus for spectral analysis of images, and particularly for analyzing an optical image of a scene to determine the spectral intensity of each pixel thereof. A spectrometer is an apparatus designed to accept light, to separate (disperse) it into its component wavelengths, and detect the spectrum. An imaging spectrometer is one which collects incident light from a scene and analyzes it to determine the spectral intensity of each pixel thereof.

The conventional imaging spectrometer includes a slit in the imaging plane for scanning the scene to be analyzed and focusing the scanned light on an array of detectors. When a two-dimensional detector array is used, one of the dimensions of the array is used to sample the different wavelengths associated with a single pixel, while the field of view is covered by a one-dimensional scanner and the remaining dimension of the array. When a one-dimensional detector array is used, the field of view is scanned mechanically in two directions, and all the detectors are used at any given time only to sample the different wavelengths of a single pixel. In both cases, the slit in the image plane ensures that each detector sees only the contribution of a single pixel at a single wavelength at any time; otherwise, it would be impossible to separate the spectra of each pixel.

However, conventional slit-type imaging spectrometers suffer from the disadvantage that most of the pixels of one frame are not measured at any given time, even though the fore optics of the spectrometer actually collects incident light from all of them simultaneously. Thus, the conventional slit-type technique is wasteful of the available information since, except for one wavelength, most of the radiation emitted by the measured pixel at any given time and reaching a particular detector are rejected. The result is that either a relatively large measurement time is required to obtain the necessary information with a given signal-to-noise ratio, or the signal-to-noise ratio (sensitivity) is substantially reduced for a given measurement time.

An object of the present invention is to provide a novel method and apparatus for spectral analysis of images which have advantages in the above respects.

More particularly, an object of the invention is to provide a method and apparatus for spectral analysis of images which better utilizes all the information available from the collected incident light of the image to substantially decrease the required frame time and/or to substantially increase the signal-to-noise ratio, as compared to the conventional "slit" type of imaging spectrometer.

SUMMARY OF THE INVENTION

According to the present invention, there is provided a method of analyzing an optical image of a scene to determine the spectral intensity of each pixel thereof, comprising: (a) collecting incident light from the scene; (b) passing the light through an interferometer which outputs modulated light corresponding to a predetermined set of linear combinations of the spectral intensity of the light emitted from each pixel; (c) focusing the light outputted from the interferometer on a detector array; and (d) processing the output of the detector array to determine the spectral intensity of each pixel thereof.

The method may be practiced by utilizing various types of interferometers, both of the moving type wherein the OPD (optical path difference) is varied to modulate the light by moving the entire interferometer or an element in the interferometer, as well as of the non-moving type wherein the OPD is varied with the angle of incidence of the incoming radiation. Thus, in the moving type interferometer, at each instant, each detector looks at a fixed point of the scene and its signal is a linear combination of the spectral content of the radiation emitted by it, which varies with time. When the scanner completes one scan of the interferometer, the scene will have been scanned at all relevant linear combinations of the spectral content. In the non-moving type interferometer, wherein the OPD varies with the angle of incidence of the incoming light, at each instant, each detector sees a different point of the scene and its signal is a different linear combination of the spectral content. When the scanner completes scanning one frame, the complete frame will have been scanned at all relevant linear combinations of the spectral content.

For purposes of illustration, the invention is described below as implemented by use of the Fabry-Perot and Michelson interferometers as examples of the moving-type interferometers, and as implemented by use of the Michelson and Sagnac interferometers as examples of the non-moving type interferometers.

The invention also provides apparatus for spectral analysis of images in accordance with the above method.

The methods and apparatus in accordance with the above features differ from the conventional slit-type imaging spectrometer by utilizing an interferometer as described above, instead of a grating or a prism., without limiting the collected energy with an aperture or slit, thereby substantially increasing the total throughput of the system. Such methods and apparatus thus better utilize all the information available from the incident light of the scene to be analyzed, thereby substantially decreasing the measuring time and/or substantially increasing the signal-to-noise ratio (sensitivity).

Consider, for example, the "whisk broom" design described in John B. Wellman, Imaging Spectrometers for Terrestrial and Planetary Remote Sensing, SPIE Proceedings, Vol. 750, p. 140 (1987).

Let n be the number of detectors in the linear array, m×m the number of pixels in a frame and T the frame time.

The total time spent on each pixel in one frame summed over all the detectors of the array is:

$$nT/m^2$$

By using the same size array and the same frame rate in a method according to the present invention, the total time spent summed over all the detectors on a particular pixel is the same, $nT/m^2$. However, whereas in the conventional grating or prism method the energy seen by every detector at any time is of the order of 1/n of the total because the wavelength resolution is 1/n of the range, in a method according to the present invention the energy is of the order of unity because the modulating function is a sinusoidal (Michelson) or similar periodic function (low finesse Airy function with Fabry-Perot) whose average over many periods is 50%. Based on the standard treatment of the Jacquinot advantage (or multiplex advantage) described in interferometry textbooks, it is possible to show that devices according to the present invention have measurement signal-to-noise ratios which are improved by a factor of $n^{0.5}$ in the infrared range (background limited performance) and by the square root of the ratio of the signal at a particular wavelength to the average signal in the spectral range, at wavelengths of a narrow peak ..in the visible range (signal photon noise limited performance). For a mathematical treatment and definition of the Fabry-Perot interferometer and a definition of the Airy Function, see Max Born and Emil Wolf, Principles of Optics, Pergamon Press, 1980, p. 329.

In all the embodiments of the invention described below, all the required optical phase differences are scanned simultaneously with the spatial scanning of the field of view in order to obtain all the information required to reconstruct the spectrum, so that the spectral information is collected simultaneously with the imaging information.

The invention can be used with many different optical configurations, such as a telescope for remote sensing, a microscope for laboratory analysis, fiber optics for industrial monitoring, and others. In addition, any wavelength range can be selected with appropriate filters and optics.

BRIEF DESCRIPTION OF THE DRAWINGS

The invention is herein described, by way of example only, with reference to the accompanying drawings, wherein:

FIG. 10 shows a modified Sagnac interferometer as in FIGS. 6 and 6A but where the scanning is effected by a movable element of the interferometer;

FIG. 11 shows an interferometer as in FIGS. 6 and 6A, but with an additional optical plate made of a light transmitting material at 90° to the beamsplitter;

FIG. 12 shows an interferometer similar to that of FIG. 11 but with a different orientation of the various components, the additional optical plate 138 is also at 90° to the beamsplitter;

DESCRIPTION OF THE PREFERRED EMBODIMENTS

Figure 1:
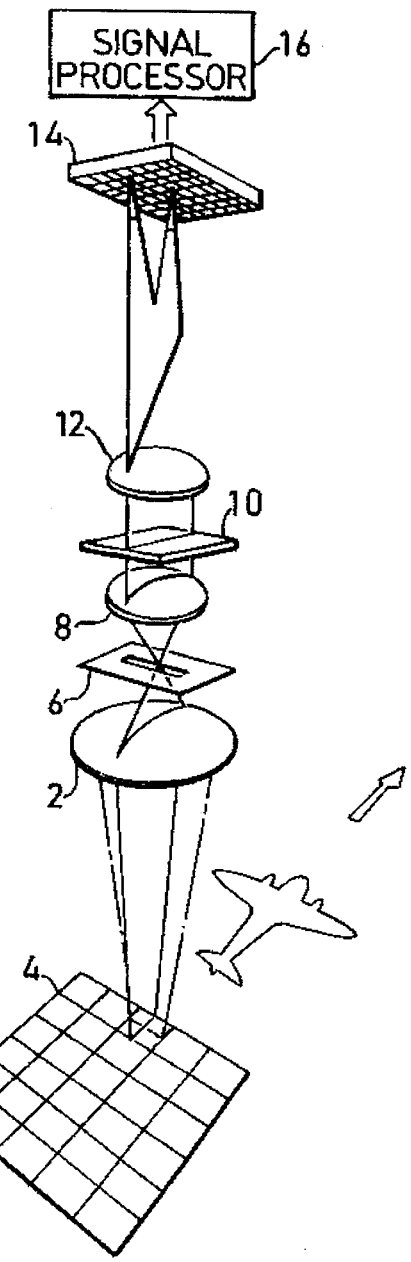
FIG. 1 illustrates a conventional (prior art) slit-type imaging spectrometer.

For purposes of better understanding the present invention, as illustrated in FIGS. 2–15 of the drawings, reference is first made to the construction and operation of a conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system, such as a telescope as indicated at 2, for collecting the incident light from the scene, schematically indicated at 4 and focusing the substantially parallel light of the scene onto a first focal plane occupied by a slit 6 to define the field of view. The light exiting from slit 6 is collimated in a collimator lens 8 and is passed through a transmission or reflection grating 10 to separate the various wavelengths. The output from grating 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., when embodied in an aircraft) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time; this is necessary to separate the spectra of each pixel.

As mentioned earlier, the disadvantage of the prior art method illustrated in FIG. 1 is that most of the pixels of one frame are not measured at any given time even though the telescope (2 or other collecting optics) actually collects energy from all of them simultaneously. As a result, the required frame time is significantly increased, and/or the signal-to-noise ratio (sensitivity) is substantially decreased with respect to a system, if it existed, which did not have the need for such a slit.

Figure 2:
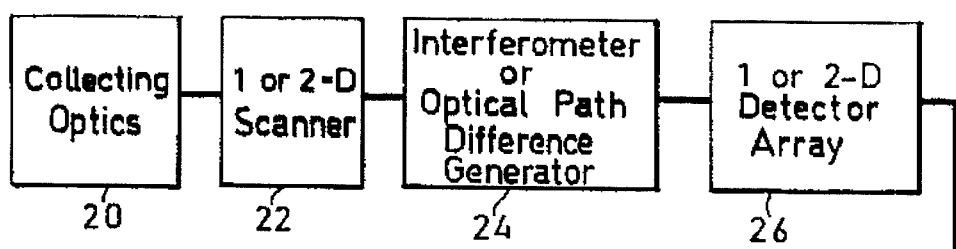
FIG. 2 is a block diagram illustrating the main components of an imaging spectrometer constructed in accordance with the present invention.

FIG. 2 is a block diagram illustrating the main components of an imaging spectrometer constructed in accordance with the present invention.

Thus, the imaging spectrometer of FIG. 2 includes: a collection optical system, generally designated 20; a one-dimensional or two-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

Throughout it is intended that the radiation, such as light, to be analyzed can come from a wide variety of sources. For example, the source may emit radiation spontaneously or reflect or transmit radiation from a lamp or other illuminated object. In addition, with proper illumination, such as UV of laser, and with proper means of preventing the illuminating wavelengths from reaching the spectral imager, fluorescence or Raman spectral imaging measurements can be performed, in order to obtain different information about the about the object or objects in question in each case.

A critical element in the novel system is the optical path difference generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously with the spatial scanning of the field of view, in order to obtain all the information required to reconstruct the spectrum. The spectrum of all the pixels in the scene is thus collected simultaneously with the imaging information, thereby permitting analysis of the image in a real-time manner.

A method and apparatus according to the present invention may be practiced in a large variety of configurations. Specifically, the interferometer used may be of either the moving or the non-moving type and the detector array may, independently of the type of interferometer, be one- or two-dimensional. When the interferometer is of the moving type and the detector array is two-dimensional, no scanning is required, except for movement of the interferometer which is an OPD scan. When the interferometer is of the moving type and the detector array is one-dimensional, spatial scanning in one dimension is required. When the interferometer is of the non-moving type and the detector array is two-dimensional, OPD scanning in one dimension is required. When the interferometer is of the non-moving type and the detector array is one-dimensional, scanning in two dimensions is required, with one dimension relating to a spatial scan while the other relates to an OPD scan.

Figure 3:
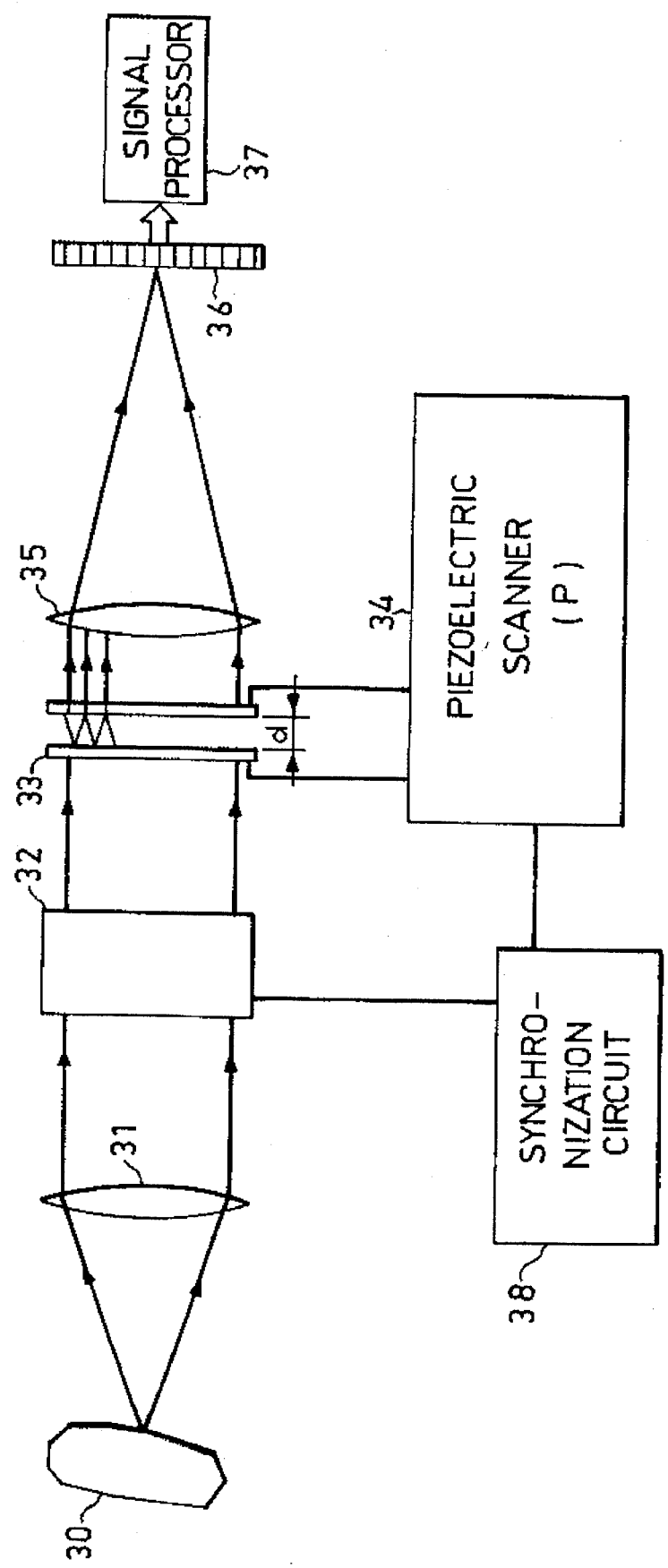
FIG. 3 is a diagram illustrating an imaging spectrometer constructed in accordance with the present invention based on the use of a moving-type interferometer, namely, a Fabry-Perot interferometer with scanned thickness.

FIG. 3 illustrates one form of imaging spectrometer constructed in accordance with the present invention. This spectrometer is based on the use of a moving type interferometer in which the OPD is varied to modulate the light, namely, a Fabry-Perot interferometer 33 with scanned thickness.

Thus, the imaging spectrometer illustrated in FIG. 3 comprises a source or scene, generally designated 30, to be analyzed to determine the spectral intensity of each pixel of the scene. The scene 30 may be a source of incoherent non-monochromatic radiation. It may be at a distance for remote-sensing applications, in which case the collection optical system, schematically indicated at 31, would be a telescope; alternatively, the scene 30 may be close for microscopic analysis, in which case the collection optical system 31 would be a microscope.

Optical system 31 provides an output to a one-dimensional mechanical scanner, e.g., a mirror scanner as indicated at 32, to scan the scene. The output from scanner 32 is fed to a Fabry-Perot interferometer 33 having an etalon made of two plane, parallel reflectors spaced at a distance "d" from each other. In this example, the spacing distance "d" is variable by using a mechanical scanner, in this case a piezoelectric scanner 34.

The output from the Fabry-Perot interferometer 33 is fed through a refocusing optical system 35 onto a one-dimensional array of detectors 36 whose outputs are fed to a signal processor 37. If a two-dimensional detector array is used, scanner 32 can be eliminated.

Optical system 31, e.g., an afocal telescope or microscope, produces a substantially parallel beam (i.e., exactly parallel or having a very large F/No) at its output, because in this way every detector within the array 36 corresponds to a single optical phase difference through the etalon 34 of the Fabry-Perot interferometer 33. The optical system 31 can be either refractive or reflective. The etalon 33 of the interferometer is at 90° to the optical axis of the system. It will be noted that no use is made of a field-of-view limiting aperture or slit. The imaging spectrometer illustrated in FIG. 3 operates as follows: A detector element i of the array 36 receives radiation from a beam which traverses the etalon 33 at a fixed angle ($\phi_i$) between its line of sight and the normal to the etalon, and therefore it sees this radiation always through an optical phase difference $\delta_i$, given by:

$$\delta_i = 2\pi 2d(n^2 - \sin^2\phi_i)^{0.5}/\lambda \quad (1)$$

where $\lambda$ is the wavelength of the radiation considered, and n is the index of refraction of the air between the plates.

The total radiation reaching detector $i_k$ at any given time from a specific pixel k of the radiation input 30 is the convolution of that pixel's spectrum with the Airy function, as follows (Max Born and Emil Wolf, Principles of Optics, Pergamon Press, 1980, page 327):

$$I_{ik} = \int \{I_k(\lambda)/(1 + F \sin^2[\delta_i(\lambda)/2])\} d\lambda \quad (2)$$

where
the integration is between $\lambda_1$ and $\lambda_2$, and
$\lambda_1, \lambda_2$ = limits of the spectral range
$I_k(\lambda)$ = spectral intensity of the source at pixel k
F = coefficient of finesse, is related to the reflectivity of the etalon R, by:

$$F = 4R/(1-R)^2$$

i = that particular detector which images pixel k through an optical phase difference $\delta_i(\lambda)$ Following is one of many ways of scanning the field of view and the thickness of the etalon 33.

Suppose the array 36 is composed of a linear set of N detectors, whose signals can be monitored simultaneously and independently. Suppose M performs a raster type scan of m lines (larger than N) and that the plane of the paper in FIG. 3 is the vertical direction. Every time M has scanned one horizontal line, the thickness "d" of the etalon 33 is incremented by the piezoelectric scanner 37 one step in synchronization with the vertical scanner 32 starting from d=0, until N lines are scanned, and N thickness steps are made. At this moment the etalon thickness is returned to the original value, and the thickness scanned again. The process is repeated until the scanner has scanned one complete frame.

Except for a marginal region of N pixels at the top and at the bottom of the field of view, all the pixels of the field of view are measured with N optical phase differences by different detectors. All the detector signals are sampled and recorded at a high rate, such that all the needed information is collected and fed to the signal processor 37 to reconstruct both the image and the spectra of all the pixels.

As mentioned above, another possible configuration is one which includes a two-dimensional array of detectors: in this case the same idea applies, but one spatial scan is saved.

For example, if the array is an N×m matrix in a "push broom" approach similar to that described on Page 142 of John B. Wellman, Imaging Spectrometers for Terrestrial and Planetary Remote Sensing, SPIE Proceedings, Vol. 750, p. 140 (1987), the N lines and m columns correspond to the same matrix in object space.

In this configuration, the Fabry-Perot thickness or optical phase difference is kept fixed for the time of integration of one line. Then the scanner performs a step vertically, and the Fabry-Perot thickness d is stepped in synchronization by one step, starting from zero, until N steps are performed. At this point the scanner continues scanning vertically, the thickness starts from zero again, and the steps are repeated until the complete field of view is scanned.

In this way all the pixels are measured through all the optical phase differences, and the recorded information is processed to yield the spectra of every pixel.

The reconstruction of the spectrum of every pixel may be done by suitable mathematical processing, as follows:

One divides the spectral range of interest $\lambda_1$ to $\lambda_2$, into N intervals. If one approximates the integral of Equation (2) as a sum over N wavelength intervals, Equation (2) is the product of an N×N dimensional matrix given by:

$$A_{ij}=1/[1+F\sin(2\delta_{ij}/2)] \qquad (3)$$

and an N dimensional vector $I_k(\lambda_j)$, where j scans the N wavelength intervals, and k is a specific pixel in the field of view. If one inverts the matrix $A_{ij}$ and multiply it by the vector $I_{ik}(i_k=1,\ldots$ to n), one obtains the vector $I_k(\lambda_j)$ which is the spectrum of pixel k.

With respect to spectral resolution, consider two quasi monochromatic sources placed at the same pixel.

Preferably, the finesse F of the Fabry-Perot interferometer 33 is in the region around F=10, because (from FIG. 7.58 of the above-cited Born and Wolf publication) one sees that in this case there is enough modulation in the Airy function, and that at the same time it does not yield very narrow lines. In fact, this configuration does not correspond to a very high wavelength resolution but it is necessary in order not to lose a significant amount of radiation between the narrow peaks of the Airy function. This is a desirable situation, since in any case, because of the imaging, a high resolution may yield too much information to handle.

The treatment of the resolution on Page 334 of the Born and Wolf publication still holds, because if one sets, $$\sin(\epsilon/4)=(\epsilon/4)-1/(F)^{0.5}=1/0.3-0.3 \qquad (4)$$

one sees that one makes an error of about 10% in approximating $\sin \epsilon/4$ with $\epsilon/4$.

So one has in this case, $$\Im=\pi/2(F)^{0.5}=5 \qquad (5)$$

and the resolving power is, $$\lambda/\Delta\lambda \sim 2\Im nd/\lambda \qquad (6)$$

In order to get an idea of the order of magnitude, and check consistency, let it be assumed that, $$N=50 \text{ detectors in the array} \qquad (7)$$

$$\Delta\lambda=3\mu/50=0.06\mu \qquad (8)$$

and, $$\lambda=2 \text{ to } 5\mu \qquad (9)$$

Therefore, d is the range, $$d=\lambda^2/\Delta\lambda(2\Im n)^{-1} \qquad (10)$$

Taking n=1 for air, Equation (10) gives, $$d=10/(0.06\times 10)=16\mu \qquad (11)$$

The range of d is such that it scans the same range of optical phase differences as the wavelength range; therefore, $$d_2/\lambda_1-d_1/\lambda_1=d/\lambda_1-d/\lambda_2 \qquad (12)$$

or $$d_2-d_1=d[1-\lambda_1/\lambda_2]=16\times 0.3=5\mu \qquad (13)$$

Therefore the thickness steps are of the order of, $$5\mu/50=0.1\mu \qquad (14)$$

In the 8 to $14\mu$ spectral range one has, $$\Delta\lambda=6/50=0.12\mu \qquad (15)$$

$$d=11^2/(0.12\times 10)=100\mu \qquad (16)$$

and, $$d_2-d_1=100[1-8/14]=43\mu \qquad (17)$$

Therefore, the steps of thickness are of the order of $1\mu$. In the visible range 0.4 to $0.8\mu$, $\Delta\lambda=0.008\mu$, and therefore, $$d=0.6^2/(0.008\times 10)=4.5\mu \qquad (18)$$

From (18)

$$d_2-d_1=4.5[1-\frac{1}{2}]=2.25\mu \qquad (19)$$

and therefore the steps in d are $$2/50=0.04\mu \qquad (20)$$

In summary, the significant features in the system illustrated in FIG. 3 include: i) the special matching of the interferometer thickness range and finesse, with the detector array size and number of detectors and the spectral resolution; and ii) the synchronization between the thickness scanning and the spatial scanning, to obtain the spectral and the spatial information simultaneously in the time one frame is built.

Many other scanning configurations may exist, which do not require synchronization. In such configurations the data-taking sequence will depend on the type of signal scanning of the detector array and on whether the detector array is one-dimensional or two-dimensional, as described above. It is intended that all such configurations fall within the scope of the present invention.

It will be seen when using the moving type interferometer as illustrated in FIG. 3, a beam entering the interferometer at a small angle ($\phi\approx 0$) to the optical axis undergoes an optical path difference which varies as $\phi^2$ or higher power of $\phi$. All the spectral information in all the pixels may be collected by scanning the optical path difference in synchronization with the scene scan, at the end of which, every pixel has been measured through all the optical path differences by different detectors. By careful bookkeeping and by applying the appropriate matrix inversion (such as Fourier transformation), the spectrum of every pixel may be calculated. The bookkeeping is needed because different detectors gather the information of different OPD's of one pixel at different times. Thus, in the time of 30 msec (the usual frame time of a standard video), a spectrum may be measured for every pixel of a standard video frame. This is of the order of 100 resolution points per pixel, with a typical matrix of 500×500 pixels per frame.

Figure 4:
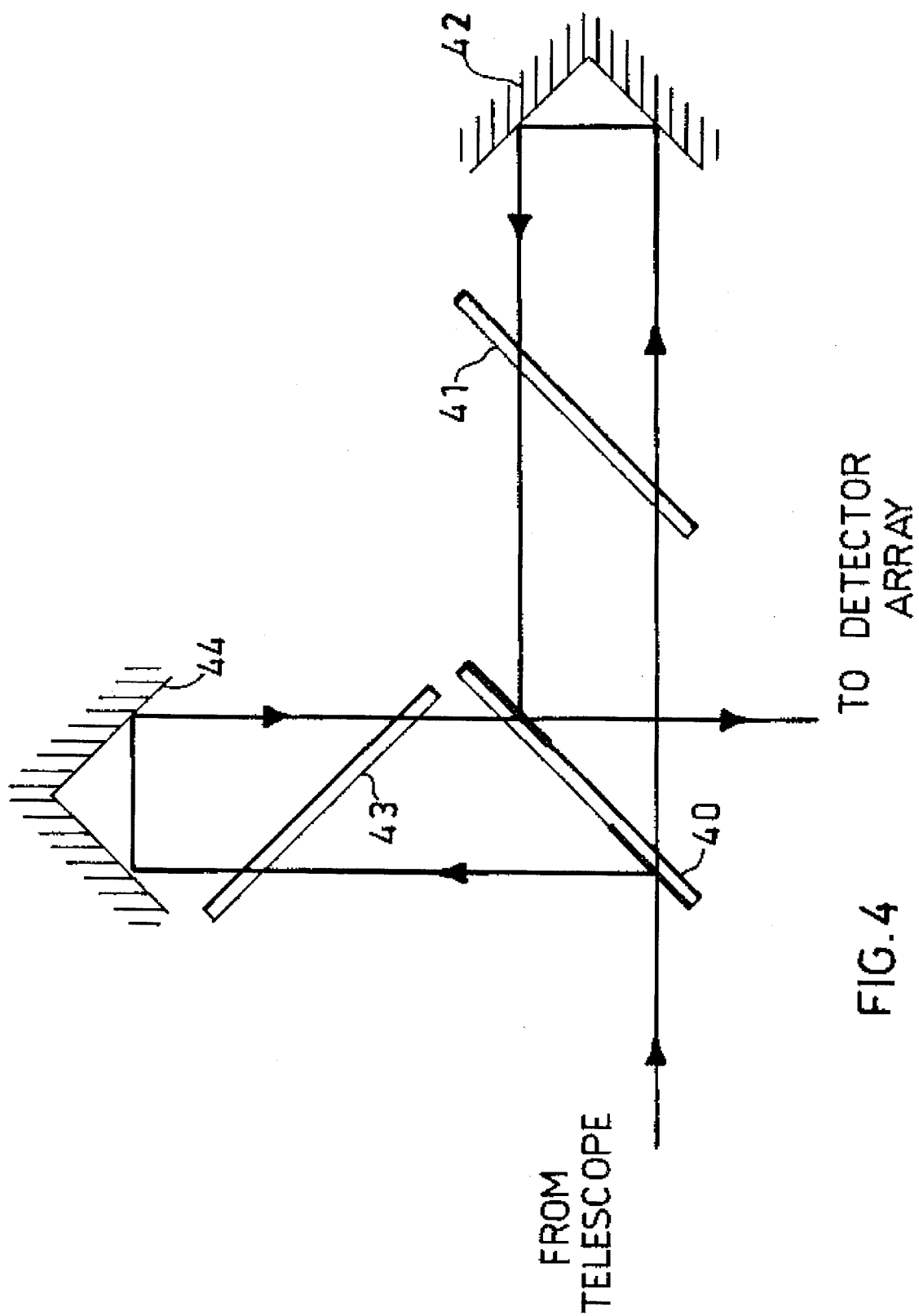
FIG. 4 illustrates a Michelson interferometer with retroreflectors used as a non-moving type interferometer in the imaging spectrometer of FIG. 2.

In the construction of FIG. 4, instead of using a moving-type interferometer wherein the OPD (optical path difference) varies by moving an element in the interferometer (namely, changing the spacing d between the plate mirrors in the Fabry-Perot interferometer illustrated in FIG. 3), the invention may also be implemented by using a non-moving type interferometer, in which case the OPD varies with the angle of incidence of the incoming radiation. FIG. 4 illustrates the invention implemented by using the latter type interferometer, namely, by using a Michelson type interferometer.

Thus, the interferometer illustrated in FIG. 4 includes a beamsplitter 40 receiving the beam from the optical collection system and scanner (31 and 32, respectively, FIG. 3), and splitting the beam into two paths. Scanner 32 may be one-dimensional or two-dimensional, depending on whether detector array 36 is two-dimensional or one-dimensional, respectively. One path includes a compensator 41 and a retroreflector 42 while the second path includes a compensator 43 and a retroreflector 44. The two compensators, 41 and 43, are identical blocks of the same material and of the same thickness, and are positioned antisymmetrically in the two arms so that only beams which are parallel to the optical axis are compensated. The two retroreflectors, 42 and 44, are positioned at equal distances from the beamsplitter 40. The beamsplitter 40 has a half-reflecting coating only on a portion of its surface on each side so that the translation of the beam through the corner cube is exploited to obtain a completely compensated system for rays parallel to the optical axis.

Thus, in the Michelson type interferometer illustrated in FIG. 4, the beam which is parallel to the optical axis of the system is compensated between the two arms of the interferometer, whereas the beams in directions which are off the optical axis of the system undergo OPD's (optical path differences) between the two arms which vary linearly with the incident angle. The differences are proportional to the angular deviation from the optical axis.

Therefore, when the collimated beams at the exit of the interferometer are focused on a detector array, such as array 36 in FIG. 3, each element of the array will receive light which underwent different OPD's between the two arms.

Thus, with compensator 41 parallel to the beamsplitter 40, and compensator 42 perpendicular to it, the optical path difference between the two arms can be shown to satisfy, for small $\phi$'s, the following relationship:

$$OPD(\phi)=2d \sin \phi_0[1-\cos\phi_0/(n^2-\sin^2\phi_0)^{0.5}]\phi \quad (21)$$

with $\phi_0$=angle between the beamsplitter 40 and the optical axis. For simplicity $\phi_0$ can be taken as 45°, but this is not essential. n is the index of refraction of the two compensators, 41 and 43, d is the compensator thickness, and $\phi$ is the angular deviation from the optical axis.

For example, if the required change in OPD between two adjacent detectors is ~1µ, and the change in directions between the fields of view of two neighboring detectors is ≈1 mrad, d turns out to be of the order of 1 mm. In fact, $$d=1\mu/\{2(2)^{0.5}/2 \; [1-((2)^{0.5}/2)/(\; 4\tfrac{1}{2})^{0.5})]10^{-3}\}=1 \text{ mm}$$

Note that if compensator 41 is removed and beamsplitter 40 is half-reflecting on the whole surface on the side of the incoming beam, then one obtains another viable configuration with a compensated optical axis.

With respect to the spectral resolution of the FIG. 4 configuration, assume that the spectral range of the radiation reaching the detector is limited to, $$\lambda_1 > \lambda > \lambda_2$$

by using a suitable filter, or because of the transmission properties of the optics.

Because of the Nyquist sampling theorem, in order to avoid aliasing, the interferogram must be sampled with OPD steps which are no larger than $\lambda_1/2$. For the purpose of illustration, one can assume that this is also the difference in OPD subtended by two adjacent detectors. Since one period is an OPD change of one wavelength, the maximum difference in OPD seen by two adjacent detector elements must be, $$\lambda_1/2$$

Assume now that the incident radiation consists of two lines at wave numbers v and v+Δv with an intensity of $I_0$. The resultant intensity for an OPD of x is:

$$I(x)=0.5I_o(1+2 \cos 2\pi vx)+0.5I_o(1+2 \cos 2\pi(v+\Delta v))x) \quad (23)$$

If one subtracts the constant term, one obtains, $$\begin{aligned} I(x) &= I(x) - I_0 \\ &= I_0[\cos(2\pi vx) + \cos\pi(v + \Delta v)x] \\ &= 2I_0[2\pi(v + \Delta v)x]\cos\pi\Delta vx \end{aligned} \quad (24)$$

Similar to the Rayleigh criterion, one defines the two line "resolved" if the ratio, $$I(x)/I(0)$$

is lower than a predetermined amount, say 0.9. This gives a condition for the maximum value of x, $x_{max}$, needed to get the defined resolution.

The value of $x_{max}$ which satisfies the above condition is:

$$\cos \pi\Delta vx_{max} > 0.9 \quad (25)$$

or, $$x_{max} \geq 0.143/\Delta v \quad (26)$$

Now let $N_d$ be the total number of the detectors in the array. Then:

$$x_{max} \geq N_d\lambda_1/2 \quad (27)$$

and, $$N_d\lambda_1/2=0.143/\Delta v \quad (28)$$

or, $$\Delta v=0.286/(\lambda_2 N_d) \quad (29)$$

For $v_2=1/\lambda_1$ $$\Delta v/v_2=\Delta v\lambda_2=(0.286/N_d)(\lambda_1/\lambda_2)$$

As a numerical example:
if $\lambda_1$=5 µm, $\lambda_2$=2 µm and $N_d$=100

$$\Delta v/v_2=0.7\%$$

In summary, the uniqueness of the system illustrated in FIG. 4 is represented by: i) the OPD is a linear function of the angle of incidence of the incoming radiation on the interferometer, so that different detectors of the array see it at different OPD's. This fact, combined with the spatial scanning and proper bookkeeping, allows the interferogram or Fourier transform of the spectrum of each pixel to be measured simultaneously with the image information. Again, the scanning in the case of a non-moving interferometer can be two-dimensional or one-dimensional, depending on whether the detector array is one-dimensional or two-dimensional, respectively.

Figure 5:
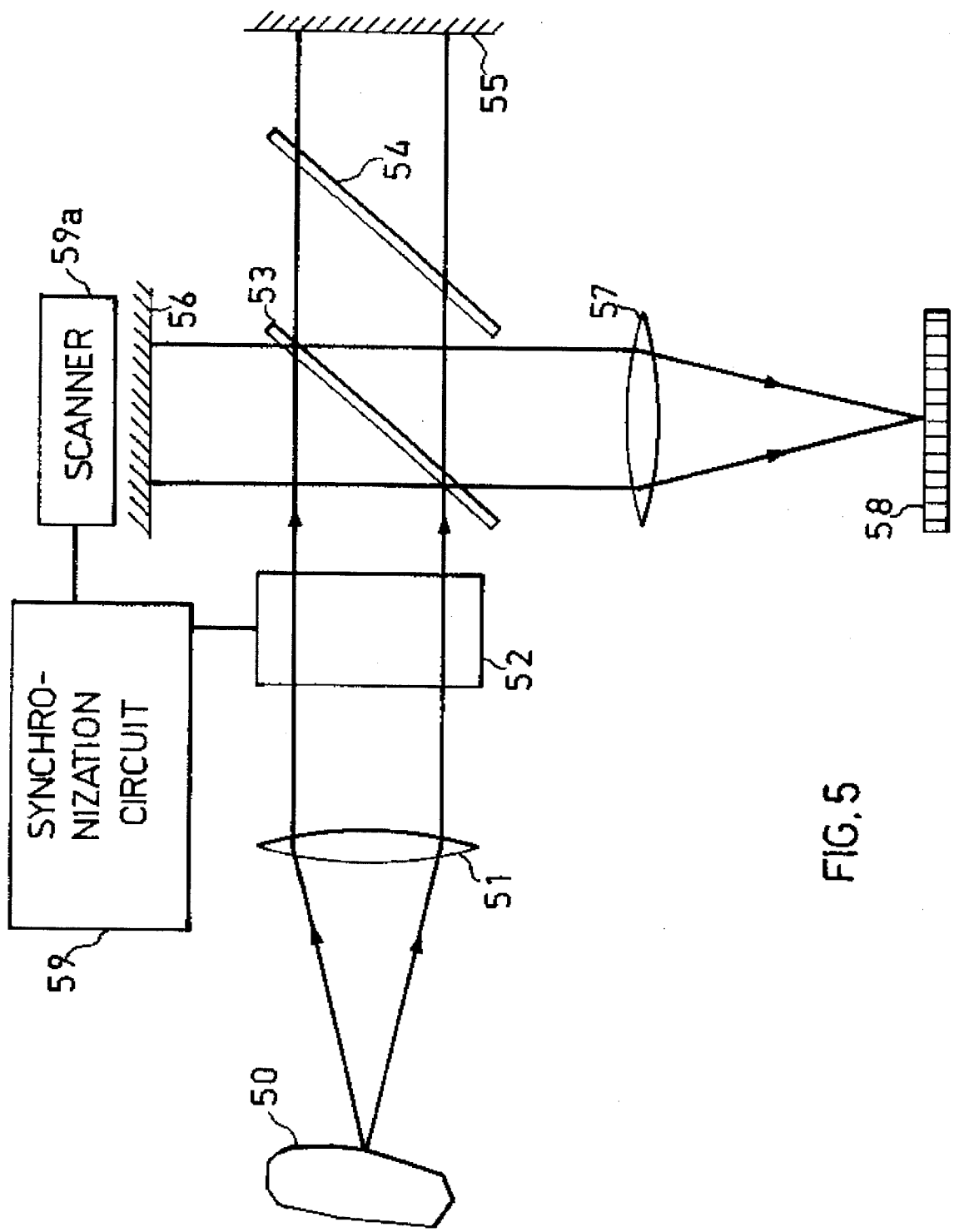
FIG. 5 is a diagram illustrating another moving-type interferometer, namely, a Michelson type interferometer, which may be used as the interferometer in the imaging spectrometer according to the present invention.

FIG. 5 illustrates an imaging spectrometer including a Michelson interferometer but of the moving type, similar to that of FIG. 3, namely, wherein the OPD varies with moving an element of the interferometer. In the spectrometer of FIG. 5, the light from source 50 is collected by the optical collection system 51 and is collimated onto a scanning mirror 52 before being passed through the beamsplitter 53 which splits the beam into the two arms. One arm includes a compensator 54 and a mirror 55, and the second arm includes merely a mirror 56. The light from the two mirrors is passed via beamsplitter 53 and a focusing lens 57 onto an array of detectors 58.

In the spectral imager illustrated in FIG. 5, if the detector array is linear then the direction of the scanning is perpendicular to the direction of the linear array and the scanning mirror 52 scans the scene in one dimension. Scanner 52 is not needed if the detector array is two-dimensional. Scanner 59a controls the distance between mirror 56 and beamsplitter 53. By scanning mirror 56 in the way of the traditional Michelson interferometer, while mirror 55 is stationary, the OPD of the two arms is varied simultaneously for all pixels in the scene. The compensator 54 ensures that the central beam has an OPD equal to zero. Many different scanning configurations and sequences may be possible, including ones in which the synchronization is not needed while the image scanner is or is not needed, depending on the whether the detector array is one-dimensional or two-dimensional.

Figure 6:
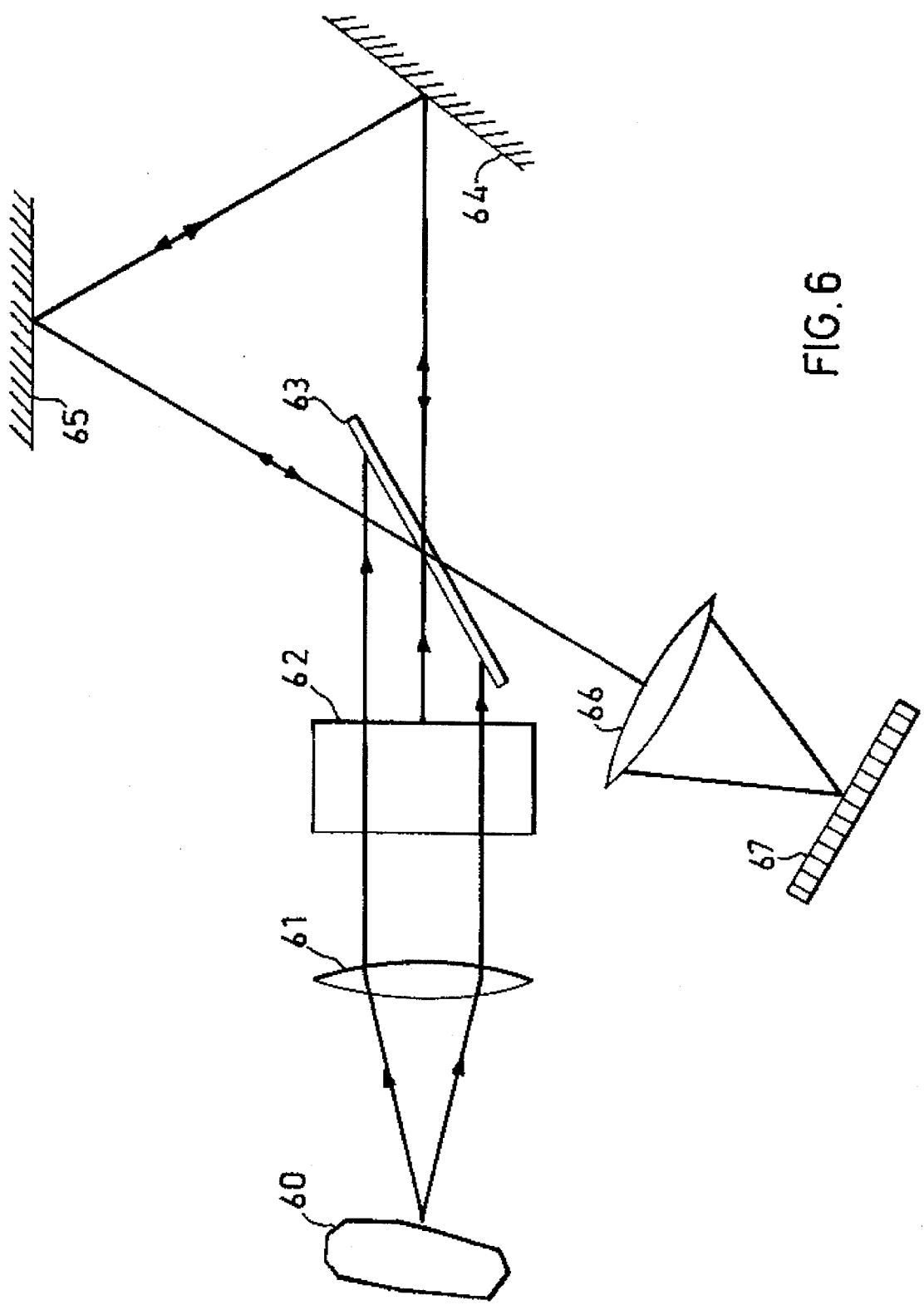
FIG. 6 illustrates another non-moving type interferometer, namely, a modified Sagnac interferometer, as used in an imaging spectrometer in accordance with the invention.

FIG. 6 illustrates an imaging spectrometer constructed in accordance with the present invention but utilizing another type interferometer, namely, a modified Sagnac, of the non-moving type in that the OPD varies with the angle of incidence of the incoming radiation. As described above with respect to the imaging spectrometer illustrated in FIG. 4, a beam entering the interferometer at a small angle to the optical axis undergoes an OPD which varies linearly with this angle.

The modified Sagnac interferometer illustrated in the spectrometer of FIG. 6 is that described in D. E, Hecht, Optics, Addison-Wesley Publishing Company, p. 359 (1987). In this interferometer, all the radiation from source 60 in all the pixels, after being collimated by the optical collection system 61, is scanned by a mechanical scanner 62. The light is then passed through a beamsplitter 63 to a first reflector 64 and then to a second reflector 65, which reflects the light back through the beamsplitter 63 and then through a focusing lens 66 to an array of detectors 67. This beam interferes with the beam which is reflected by 63, then by 65, and finally by reflector 64. With a one-dimensional array, a two-dimensional scan is required while with a two-dimensional detector array, only a one-dimensional scan is required.

At the end of one scan, every pixel has been measured through all the OPD's by different detectors at different times, and therefore the spectrum can be reconstructed by Fourier transformation. A beam parallel to the optical axis is compensated, and a beam at an angle ($\phi$) to the optical axis undergoes an OPD which is a function of the thickness of the beamsplitter 63, its index of refraction, and the angle $\phi$. The OPD is proportional to $\phi$ for small angles. By applying the appropriate inversion, and by careful bookkeeping, the spectrum of every pixel is calculated.

Figure 6A:
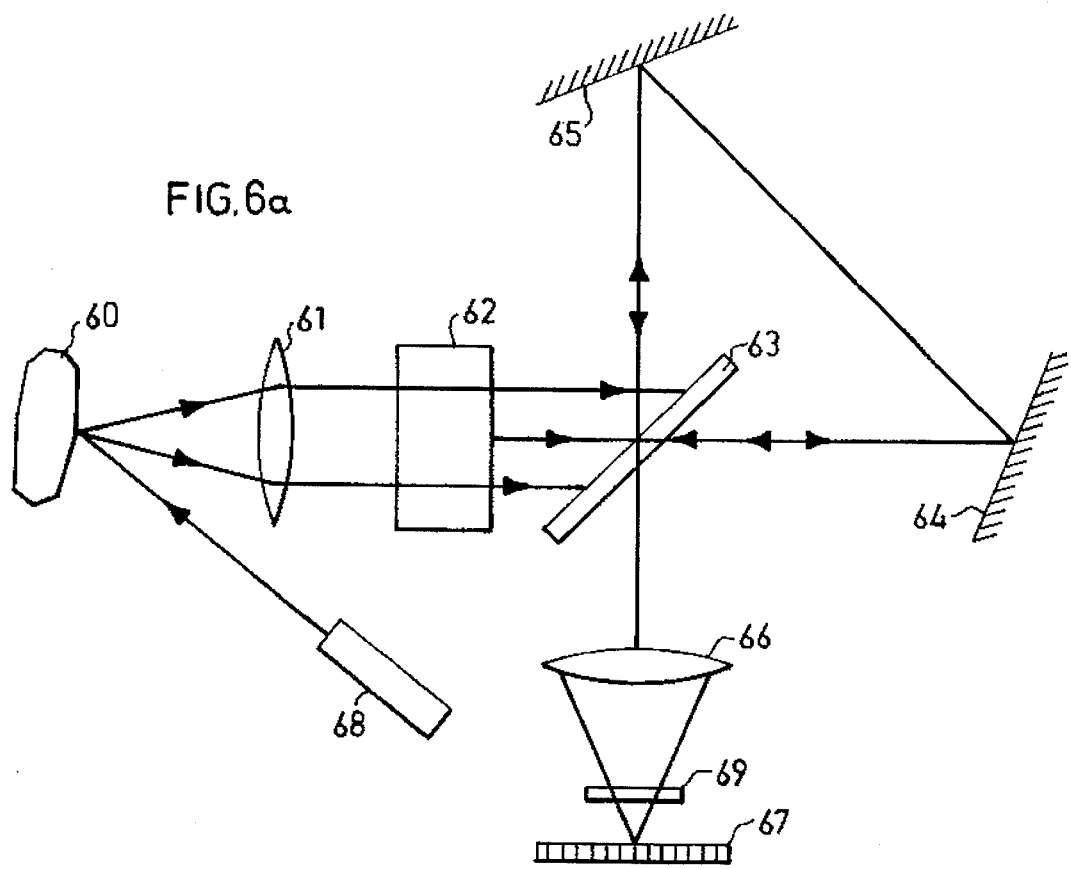
FIG. 6A illustrates yet another non-moving type interferometer, namely, a modified Sagnac interferometer, as used in an imaging spectrometer in accordance with the invention.
Figure 7:
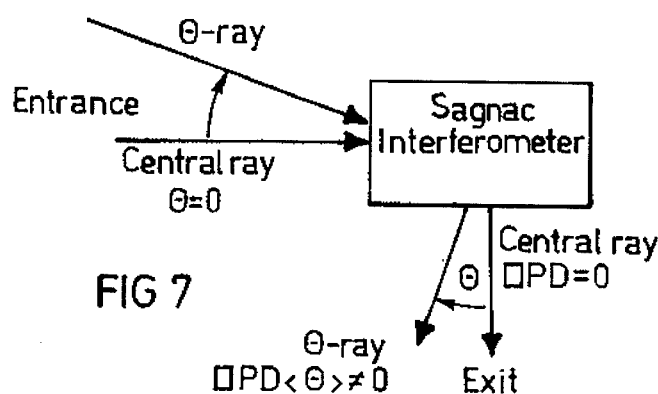
FIG. 7 schematically demonstrates that the rotation of a ray at the entrance to an interferometer such as that of FIGS. 6 and 6A also rotates the ray at the output by the same angle and changes the OPD between the corresponding split beams.

Referring to FIG. 6A, which shows a slightly modified version of the system of FIG. 6, the beam, including the central beam on the optical axis and other parallel beams at non-zero angles with respect to it within the instrument's field of view, enters the interferometer and is split into two coherent beams by the beamsplitter 63. The two split beams are rejoined after being folded by mirrors, 64 and 65, and create interference patterns on the detector array 67 where they are focused by focusing lens 66.

The various configurations described herein can be adapted, where necessary, to accommodate various types of illumination. FIG. 6A can be used to illustrate this concept. For example, in the case of fluorescence radiation, a laser or UV lamp 68 is used to illuminate source 60. The induced fluorescence spectrum emitted by source 60 is then measured by the spectral imager. It is to be noted that since in fluorescence the amount of emitted is typically quite small compared to the incident light, a notch filter 69 is placed in front of detector array 67, or in any other suitable location.

The function of notch filter 69 is to block the scattered or reflected radiation of the laser or lamp itself. The blocking is necessary to prevent the flooding of detector array 67 with undesired signals. The function of notch filter 69 can alternatively be fulfilled by any suitable type of filter which is capable of cutting off the reflected or scattered light from the lamp. In the case of a UV lamp, the lamp itself typically includes a cut-off filter which limits the spectral range of the light incident upon the sample. In addition, since the fluorescent light is usually weak, cooled or intensified detector arrays may be used to increase the signal to noise ratio of the measurement.

In Raman spectroscopy application the situation is as with fluorescence except that a laser 68 is used. The radiation source may be placed as in FIG. 6A for reflection analysis. In the case of transmission analysis, the radiation source would be placed behind source 60, i.e., to the left of source 60 in FIG. 6A.

The scanning between the scene and the interferometer fringes can be performed either by using a scanner external to the interferometer (moving scene) or by rotating the interferometer itself (moving fringes). This can be better understood with reference to FIG. 7 where it is seen that any ray, for example the central ray shown in the FIG., which is rotated by an angle $\theta$ at the entrance of the Sagnac interferometer, is rotated at the output by the same angle. However, the OPD between the corresponding split beams is changed.

Figure 8:
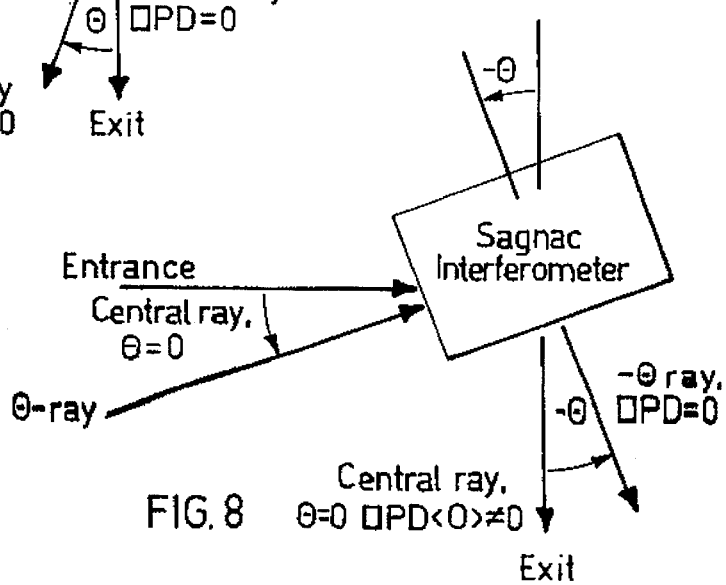
FIG. 8 schematically demonstrates that the same effect as demonstrated in FIG. 7 can be achieved through the rotation of the interferometer.

Similarly, with reference to FIG. 8, rotating the Sagnac interferometer by an angle $\theta$ leaves the outgoing beam fixed in space but changes the OPD by the same amount as before.

In the Sagnac configurations of FIG. 6 and FIG. 6A, the ray which is incident on the beamsplitter at an angle $\beta$ ($\beta=60°$ in FIG. 6 and 45° in FIG. 6A) goes through the interferometer with an OPD=0, whereas a ray which is incident at a general angle $\beta-\theta$ undergoes an OPD given by the following:

$$OPD(\beta,\theta,t,n)=t[(n^2-\sin^2(\beta+\theta))^{0.5}-(n^2-\sin^2(\beta-\theta))^{0.5}+2\sin\beta\sin\theta]  \quad (30)$$

where, $\beta$=is the angle of incidence of the ray on the beamsplitter ((60° in FIG. 6 and 45° in FIG. 6A)

$\theta$=the angular distance of a ray from the optical axis or Sagnac rotation angle with respect to the central position t=the thickness of the beamsplitter n=the index of refraction of the beamsplitter Equation (30) may be approximated by the linear equation:

$$OPD(\beta,\theta,t,n)=2t\sin\beta[1-(n^2-\sin 2\beta)^{-0.5}\cos\beta]\theta \qquad (31)$$

What follows is valid also for the configuration of FIG. 4 and Equation (21).

It follows from Equation (30) that by scanning both positive and negative angles with respect to the central position, one can get a double-sided interferogram for every pixel, which helps eliminate phase errors giving more accurate results in the Fourier Transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the Nyquist theorem, this OPD step must be smaller than half the shortest wavelength to which the system is sensitive.

Another parameter which should be taken into account is the finite size of a detector element in the matrix. Through the focusing optics, the element subtends a finite OPD in the Sagnac interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the Modulation Transfer Function (MTF) condition is satisfied, i.e., that the OPD subtended by a detector element in the interferometer must be smaller than the shortest wavelength at which the instrument is sensitive.

Figure 9:
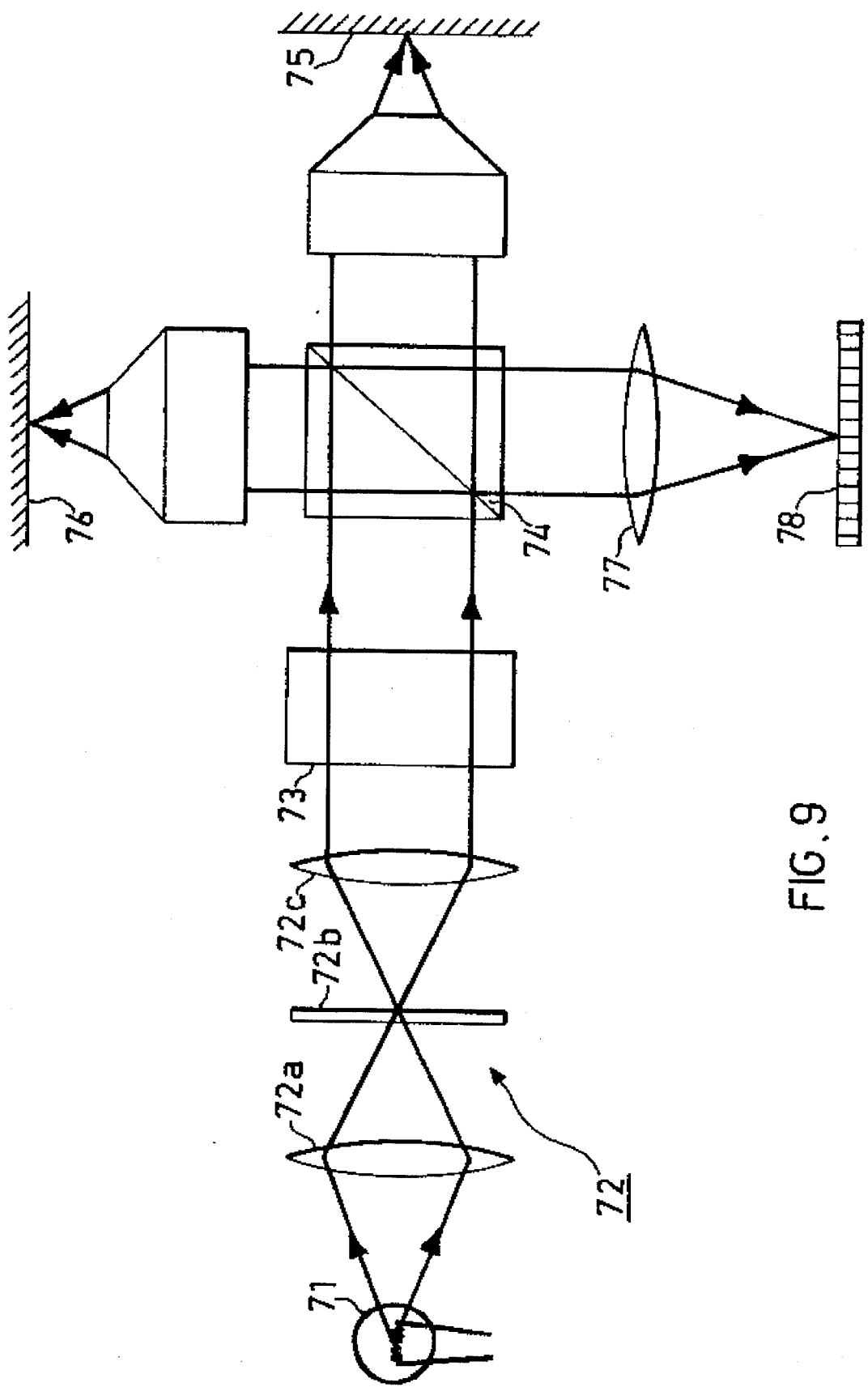
FIG. 9 illustrates the invention as embodied in a modified Michelson imaging spectrometer, as an example of another moving type interferometer, with focusing on the mirrors through microscope objectives.

FIG. 9 illustrates an additional imaging spectrometer including a Michelson interferometer of the moving type, similar to that illustrated in FIG. 5, but constructed so that the light is focused on the reflectors through microscope objectives. Thus, the spectrometer illustrated in FIG. 9 includes a light source 71 and a microscope optical system 72 including a condenser lens 72a, for focusing on the object 72b. Optical system 72 further includes a collimator lens 72c for directing the light through a scanner 73, through a beamsplitter 74 to the two reflectors, 75 and 76, and then through a focusing lens 77 onto a detector array 78. The detector array 78 in configuration of FIG. 9, as well as in the previously-described configurations, may be a CCD (charge coupled device).

The scanner 73 scans the field of view in one dimension if the detector array is one-dimensional. It is not needed at all if the detector array is two-dimensional. Reflector 75 and the microscope system move together along the optical axis to provide scanning of the OPD in synchronization with the scanner 73 (if present), as described above with respect to FIG. 5.

As described above, the OPD for every pixel can be scanned in two ways:

(1) A fixed type interferometer is used, in which the interferometer is kept in a fixed position, and the scene is scanned with an optical scanner. Since each detector in the detector array sits in a position on the focal plane from which it sees the radiation through a fixed OPD, which OPD varies from detector to detector, scanning the scene ensures that each pixel is seen by all the detectors, and therefore through all the OPD's at the end of the scan. At the end of the scan, the Fourier Transformation can be applied to all the pixels; and (2) A moving type interferometer is used, wherein the scene is kept fixed, and an element in the interferometer or the whole interferometer itself is scanned in such a way that now each detector always sees the same pixel, but through different OPD's at different times. At the end of the scan, all the pixels will have been measured through all the OPD's. The Fourier Transformation can therefore be applied to the signal function measured by every detector.

Where the detector is a linear array, a one-dimensional optical scan of the scene must be added to the interferometer scan, if the entire scene is to be analyzed. In the case of a line scanner (where the scene is a line instead of an area), no additional optical scan is needed, except for the interferometer, but there are many working configurations depending on the dimensionality of the detector array and the type of interferometer used.

The decision as to which method is preferable should be based in each case on the specific requirements and geometric limitations. For example, in method (1), the spectral resolution is limited by the number of detectors and by the total OPD range allowed by the geometry of the setup. In method (2), depending on the type of interferometer used, it is possible to reach very large OPD's. Since the spectral resolution attainable is higher when a higher maximum OPD is scanned, it is clear that the second method is more suitable when high resolution is required.

The embodiments of FIGS. 10–15 are based on the second method, namely, the one wherein the scene is fixed and the OPD scanning is effected by a movable element of the interferometer or the interferometer itself, and on a third method, which is based on a fixed interferometer with an additional compensating scanner mirror (single or double-sided), in order to keep the scene stationary, and scan the interference fringes across the scene. In the second and third methods, the light is passed through a moving type interferometer, in which the OPD is varied to modulate the light by moving an element of the interferometer or a compensating mirror, or the interferometer itself, such that at each instant, each detector sees a linear combination (Fourier transform) of the spectral content of the light emitted from each pixel, and it looks at a different pixel of the scene, and that when the scanner completes one scan, the complete scene will have been scanned at all relevant linear combinations of the spectral content.

In all these methods the scene must still be scanned in one dimension if the detector array is linear.

In the drawings, FIGS. 10–15 illustrate further implementations of the second method and two implementations of the third method, i.e. wherein the scene is kept fixed and the interference fringes scan the scene.

FIG. 10 illustrates an imaging spectrometer of a type similar to the modified Sagnac interferometer illustrated in FIG. 6, except that it is based on method (2) described above, namely, effecting the scanning by a movable element of the interferometer, rather than method (1) above, wherein scanning is effected by scanning the image.

Thus, the imaging spectrometer illustrated in FIG. 10 is similar to that illustrated in FIG. 6, in that it includes an optical image source 110 in which all the spectral information in all its pixels, after being collimated by the optical collection system 111, is scanned by a mechanical scanner 112. This scanner is needed only if the detector array is linear. If it is two-dimensional, it is not needed. The light is then passed through a beamsplitter 113 to a first reflector 114, and then to a second reflector 115, which reflects the light back through the beamsplitter 113 and then through a focusing lens 116 to a detector array 117. In the apparatus illustrated in FIG. 10, however, the beamsplitter 113 is rotated about an axis perpendicular to the optical path (and perpendicular to the paper) to effect the scanning. Thus, this rotation of the beamsplitter changes the OPD through which a collimated beam from a pixel reaches a specific detector, without changing the detector on which it is focused. It is thus clear that a scan of the beamsplitter angle with respect to the optical axis causes every pixel to be scanned through an OPD range.

Thus, in method (2) above (scanning being effected by the interferometer), when one looks at the focal plane where the detector is placed, one can see that the image of the scene is superimposed on a number of moving interference fringes, or alternates between dark and bright scene, depending on the type of interferometer. In method (1) above (the scene scanning method), one can see that, as the optical scanner moves, the image of the scene scans through the focal plane, while the fringes remain stationary on this plane. Therefore, each point on the scene goes through positions on the focal plane, which correspond to different OPD's. At the end of one scan, all the needed information is collected for each pixel. The results of the two methods are therefore similar, but the arrangements based on the second method, provide a number of advantages as described above.

FIG. 11 illustrates an imaging spectrometer similar to that of FIG. 10 above or to FIG. 6, except that it includes an optical plate 128 of a light-transmitting material, which increases the maximum OPD, and thereby increases the spectral resolution of the apparatus. In this case, the optical plate 128 is located between the beamsplitter 123 and the second reflector 125, which reflects the light from the first reflector 124 back through the beamsplitter 123 and then through a focusing lens 126 to the detector array 127.

FIG. 12 illustrates an imaging spectrometer very similar to that of FIG. 2, except for a slightly different orientation of the first reflector 134, the second reflector 135, the optical plate 138, the beamsplitter 133, and the detector array 137 including its focusing lens 136.

Figure 13:
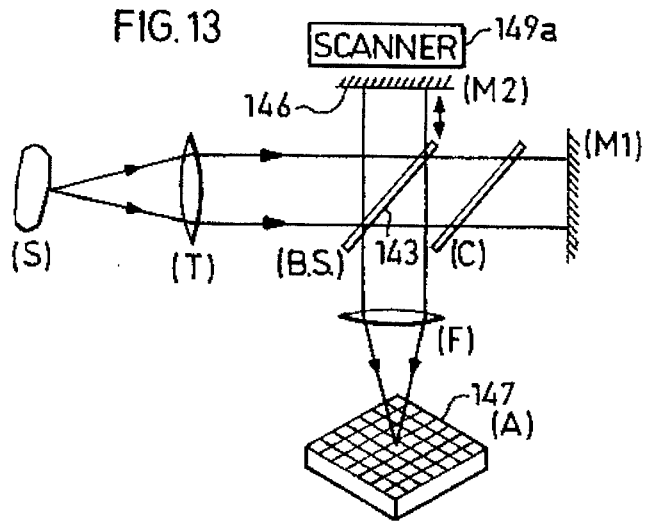
FIG. 13 shows a Michelson-type interferometer similar to that shown in FIG. 5 but with a two-dimensional detector array.

FIG. 13 illustrates an imaging spectrometer including an interferometer of the Michelson type, similar to FIG. 5. In this case, however, a two-dimensional detector array 147 is used, and therefore, a one-dimensional scanning is sufficient, rather than a two-dimensional scanning as in the apparatus illustrated in FIG. 5. Thus, in FIG. 13, the scanning is effected by mirror 146 controlled by scanner 149a, to change the distance between the mirror and the beamsplitter 143, and thereby to vary the OPD. Thus, the system illustrated in FIG. 13 obviates the need for the synchronization circuit 59 and scanning mirror 52 included in FIG. 5.

Figure 14:
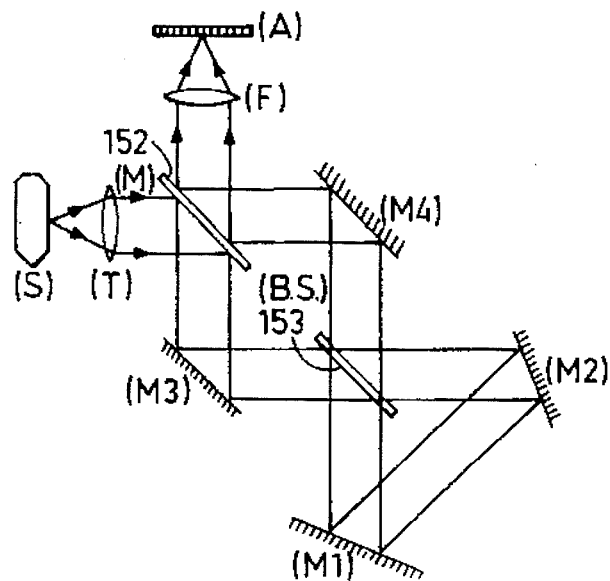
FIG. 14 shows a Sagnac interferometer as in FIG. 1 but with a scanning mirror rather than a beamsplitter.
Figure 15:
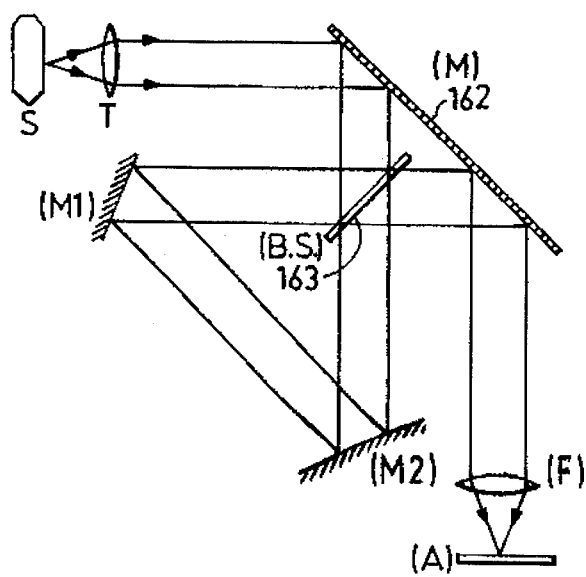
FIG. 15 is similar to FIG. 14 except that the scanning mirror is single-sided.

FIGS. 14 and 15 illustrate two further embodiments of the invention which provide advantages over the embodiment illustrated in FIG. 10. Thus, in the apparatus illustrated in FIG. 10, based on the Sagnac interferometer with rotating beamsplitter, the distance between fringes varies as a function of beamsplitter angle. This makes the transformation algorithm inconvenient and difficult to use. In the embodiments illustrated in FIGS. 14 and 15, however, the fringes scan the image without changing the distance between them. In this way, a constant fringe distance is attained, with the possibility of reaching higher spectral resolution and easier algorithm.

FIG. 14 illustrates an apparatus based on the Sagnac interferometer including a scanning mirror 152 and a beamsplitter 153. In this case, however, the scanning mirror 152, rather than the beamsplitter 153, is rotated about an axis perpendicular to the optical path (and perpendicular to the plane of the paper) to effect the scanning. As shown in FIG. 14, mirror 152 is a double-sided mirror.

FIG. 15 illustrates a similar arrangement as in FIG. 14, except that the scanning mirror 162 is single-sided and is rotated, as mirror 152 in FIG. 14, to effect the OPD scanning via the beamsplitter 163.

In FIGS. 14 and 15 the interferometer is not moving, but it works as in the moving case because of the particular arrangement of the scanning mirrors.

Further variations, modifications and applications of the invention will be apparent.

It will thus be seen that imaging spectrometers constructed in accordance with the present invention do not merely measure the intensity of light coming from every pixel in the field of view, but also measure the spectrum of each pixel in a predefined wavelength range. They also better utilize all the radiation emitted by each pixel in the field of view at any given time, and therefore permit a significant decrease in the frame time and/or a significant increase in the sensitivity of the spectrometer. Such imaging spectrometers may include other types of interferometers and optical collection and focusing systems, and may be used in a wide variety of applications, including medical diagnostic applications, remote sensing for geological and agricultural investigations, and the like.

While the invention has been described with respect to a limited number of embodiments, it will be appreciated that many variations, modifications and other applications of the invention may be made.

What is claimed is:

1. A method for simultaneously measuring the spectral intensity as a function of wavelength of all the pixels of a two-dimensional scene while detecting a real and stationary image of said scene, said method comprising the steps of:
   (a) collecting incident light simultaneously from all points of the two-dimensional scene using collimating optics;
   (b) passing said incident collimated light through an interferometer system having a number of elements, so that said light is first split into two coherent beams which travel in different directions inside said interferometer and then said two coherent beams recombine to interfere with each other to form an exiting light;
   (c) passing said exiting light through a focusing optical system which focuses said exiting light on a detector having a two dimensional array of detector elements, so that at each instant each of said detector elements is the image of one and always the same pixel of said scene for the entire duration of the measurement, so that the real image of the scene is stationary on the plane of the detector array at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
   (d) rotating one or more of said elements of said interferometer system, so that said optical path difference between said two coherent beams generated by said interferometer system is scanned simultaneously for all said pixels of the scene; and
   (e) recording said signals of each of said detector elements as function of time using a recording device.

2. The method of claim 1, wherein said incident light, prior to entering said interferometer system, is passed through an afocal telescope which simultaneously collects and collimates said light for each of said pixels of the scene.

3. The method of claim 1, wherein said incident light, prior to entering said interferometer system, is passed through a microscope which simultaneously collects and collimates said light for each of said pixels of the scene.

4. The method of claim 1, wherein said one or more elements of said interferometer system include two mirrors and one beamsplitter, and the optical path difference is scanned by rigidly rotating said beamsplitter and said two mirrors as a single element around an axis perpendicular to a plane formed by said two coherent beams, said beamsplitter and said two interferometer mirrors rotating rigidly to ensure a fixed image of the scene on said array of detector elements during said optical path difference scan.

5. The method of claim 3, wherein said one or more elements of said interferometer system include two mirrors and one beamsplitter, and the optical path difference is scanned by rigidly rotating said beamsplitter and said two mirrors as a single element around an axis perpendicular to a plane formed by said two coherent beams, said beamsplitter and said two interferometer mirrors rotating rigidly to ensure a fixed image of the scene on said array of detector elements during said optical path difference scan.

6. The method of claim 3, wherein said one or more elements of said interferometer system include two mirrors and one beamsplitter and the optical path difference is scanned by rigidly rotating said beamsplitter and said two mirrors as a single element around an axis perpendicular to a plane formed by said two coherent beams, said beamsplitter and said two interferometer mirrors rotating rigidly to ensure a fixed image of the scene on said array of detector elements during said optical path difference scan.

7. The method as in claim 1, wherein said interferometer system further includes a double sided mirror having a first side and a second side and two periscope mirrors, and wherein the optical path difference is scanned by rotating said double sided mirror around an axis perpendicular to a plane formed by said two coherent beams, such that said incident collimated light from the scene first encounters said first side of said double sided mirror, then encounters said first one of said two periscope mirrors, then encounters said beamsplitter and said two mirrors, at the exit said two coherent beams recombine, said combined beam then encountering said second periscope mirror, and then encountering said second side of said double sided mirror prior to being focused on said array of detector elements.

8. The method as in claim 2, wherein said interferometer system further includes a double sided mirror having a first side and a second side and two periscope mirrors, and wherein the optical path difference is scanned by rotating said double sided mirror around an axis perpendicular to a plane formed by said two coherent beams, such that said incident collimated light from the scene first encounters said first side of said double sided mirror, then encounters said first one of said two periscope mirrors, then encounters said beamsplitter and said two mirrors, at the exit said two coherent beams recombine, said combined beam then encountering said second periscope mirror, and then encountering said second side of said double sided mirror prior to being focused on said array of detector elements.

9. The method of claim 3, wherein said interferometer system further includes a double sided mirror having a first side and a second side and two periscope mirrors, and wherein the optical path difference is scanned by rotating said double sided mirror around an axis perpendicular to a plane formed by said two coherent beams, such that said incident collimated light from the scene first encounters said first side of said double sided mirror, then encounters said first one of said two periscope mirrors, then encounters said beamsplitter and said two mirrors, at the exit of which said two coherent beams recombine, said combined beam then encountering said second periscope mirror, and then encountering said second side of said double sided mirror prior to being focused on said array of detector elements.

10. The method of claim 1, wherein the interferometer system further includes a single large mirror, and wherein the optical path difference is simultaneously scanned for all the pixels of the scene by rotating said large mirror around an axis perpendicular to a plane formed by said two coherent beams, such that said incident collimated light from the scene first encounters said large mirror, said light then being split and recombined in said beamsplitter and said two mirrors, at the exit of which said light is reflected by said large mirror, prior to being focused on said array of detector elements.

11. The method of claim 2, wherein the interferometer system further includes a single large mirror, and wherein the optical path difference is simultaneously scanned for all the pixels of the scene by rotating said large mirror around an axis perpendicular to a plane formed by said two coherent beams, such that said incident collimated light from the scene first encounters said large mirror, said light then being split and recombined in said beamsplitter and said two mirrors, at the exit of which said light is reflected by said large mirror, prior to being focused on said array of detector elements.

12. The method of claim 3, wherein the interferometer system further includes a single large mirror, and wherein the optical path difference is simultaneously scanned for all the pixels of the scene by rotating said large mirror around an axis perpendicular to a plane formed by said two coherent beams, such that said incident collimated light from the scene first encounters said large mirror, said light then being split and recombined in said beamsplitter and said two mirrors, at the exit of which said light is reflected by said large mirror, prior to being focused on said array of detector elements.

13. The method of claim 4, wherein beamsplitter and said two mirrors are combined in a single rigid element shaped as a prism.

14. The method of claim 5, wherein beamsplitter and said two mirrors are combined in a single rigid element shaped as a prism.

15. The method of claim 6, wherein beamsplitter and said two mirrors are combined in a single rigid element shaped as a prism.

16. The method of claim 1, further comprising additional electronic means, automatically and simultaneously transferring all data in real time from all said elements of said detector array to a computer for display of a scene image on a screen for the purposes of focusing, tracking and monitoring the scene, recording intensities of said detector elements as a function of optical path difference, and computing spectra of all said pixels.

17. An apparatus for simultaneously measuring the spectral intensity as a function of wavelength of all the pixels of a two-dimensional scene while detecting a real and stationary image of said scene, said method comprising the steps of:

(a) an interferometer system for receiving collected incident collimated light simultaneously from all points of the two-dimensional scene, said light being first split into two coherent beams which travel in different directions inside said interferometer and then said two coherent beams recombine to interfere with each other to form an exiting light, said interferometer system having a number of elements, said element being rotatable so that an optical path difference between said two coherent beams generated by said interferometer system is scanned simultaneously for all said pixels of the scene;

(b) a focusing optical system through which said exiting light is passed to form a focused light;

(c) a detector having a two-dimensional array of detector elements on which said focused light is directed, so that at each instant each of said detector elements is the image of one and always the same pixel of said scene for the entire duration of the measurement, so that the real image of the scene is stationary on the plane of the detector array and so that each of said detector elements produces a signal which is a particular linear combination of light intensity emitted by said pixel at different wavelengths, wherein said linear combination is a function of the instantaneous optical path difference; and (d) recording mechanism for receiving said signals of each of said detector elements as function of time using a recording device.

18. A method for simultaneously measuring the spectral intensity as a function of wavelength of all the pixels of a two-dimensional scene located at infinity while detecting a real and stationary image of said scene, said method comprising the steps of:

(a) collecting naturally collimated incident light simultaneously from all points of the two-dimensional scene;

(b) passing said incident naturally collimated light through an interferometer system having a number of elements, so that said light is first split into two coherent beams which travel in different directions inside said interferometer and then said two coherent beams recombine to interfere with each other to form an exiting light;

(c) passing said exiting light through a focusing optical system which focuses said exiting light on a detector having a two-dimensional array of detector elements, so that at each instant each of said detector elements is the image of one and always the same pixel of said scene for the entire duration of the measurement, so that the real image of the scene is stationary on the plane of the detector array at any time during the measurement the image is still visible and recognizable, and so that each of said detector elements produces a signal which is a particular linear combination of light intensity emitted by said pixel at different wavelengths, wherein said linear combination is a function of the instantaneous optical path difference;

(d) rotating one or more of said elements of said interferometer system, so that said optical path difference between said two coherent beams generated by said interferometer system is scanned simultaneously for all said pixels of the scene; and (e) recording said signals of each of said detector elements as function of time using a recording device.

19. The method of claim 18, wherein said one or more elements of said interferometer system include two mirrors and one beamsplitter, and the optical path difference is scanned by rigidly rotating said beamsplitter and said two mirrors as a single element around an axis perpendicular to a plane formed by said two coherent beams, said beamsplitter and said two interferometer mirrors rotating rigidly to ensure a fixed image of the scene on said array of detector elements during said optical path difference scan.

20. The method as in claim 18, wherein said interferometer system further includes a double sided mirror having a first side and a second side and two periscope mirrors, and wherein the optical path difference is scanned by rotating said double sided mirror around an axis perpendicular to a plane formed by said two coherent beams, such that said incident naturally collimated light from the scene first encounters said first side of said double sided mirror, then encounters said first one of said two periscope mirrors, then encounters said beamsplitter and said two mirrors, at the exit said two coherent beams recombine, said combined beam then encountering said second periscope mirror, and then encountering said second side of said double sided mirror prior to being focused on said array of detector elements.

21. The method of claim 18, wherein the interferometer system further includes a single large mirror, and wherein the optical path difference is simultaneously scanned for all the pixels of the scene by rotating said large mirror around an axis perpendicular to a plane formed by said two coherent beams, such that said incident naturally collimated light from the scene first encounters said large mirror, said light then being split and recombined in said beamsplitter and said two mirrors, at the exit of which said light is reflected by said large mirror, prior to being focused on said array of detector elements.

22. The method of claim 19, wherein beamsplitter and said two mirrors are combined in a single rigid element shaped as a prism.

* * * * *